(12) United States Patent
Jomaa et al.

(10) Patent No.: US 10,172,823 B1
(45) Date of Patent: *Jan. 8, 2019

(54) METHOD FOR INHIBITING CANCER CELL GROWTH WITH A TRANSPLATIN COMPLEX

(71) Applicant: KING FAHD UNIVERSITY OF PETROLEUM AND MINERALS, Dhahran (SA)

(72) Inventors: Mohammed Y. Jomaa, Dhahran (SA); Muhammad Altaf, Dhahran (SA); Anvarhusein A. Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,174

(22) Filed: Apr. 30, 2018

Related U.S. Application Data

(63) Continuation of application No. 15/715,964, filed on Sep. 26, 2017, now Pat. No. 9,974,765.

(51) Int. Cl.
  *A61K 31/282* (2006.01)
  *A61K 31/4178* (2006.01)
  *C07F 15/00* (2006.01)

(52) U.S. Cl.
  CPC ........ *A61K 31/282* (2013.01); *A61K 31/4178* (2013.01); *C07F 15/0093* (2013.01)

(58) Field of Classification Search
  CPC .......................... A61K 31/282; C07F 15/0093
  See application file for complete search history.

(56) References Cited

U.S. PATENT DOCUMENTS

| 9,481,699 B1 | 11/2016 | Altaf |
| 9,840,528 B2 | 12/2017 | Altaf |
| 9,974,765 B1 * | 5/2018 | Jomaa ................ A61K 31/282 |

OTHER PUBLICATIONS

Song Liu, et al., "Theoretical study of the electron-donating effects of thiourea ligands in catalysis", Journal of Molecular Structure, vol. 1074, 2014, pp. 527-533 (Abstract only).
Seerat-ur-Rehman, et al., "Synthesis, crystal structure and antimicrobial studies of a thione derivative of transplatin, trans-[Pt(NH$_3$)$_2$(Diaz)$_2$]Cl$_2$•2H$_2$O (Diaz=1,3-diazinane-2-thione)", Inorganic Chemistry Communications, vol. 36, 2013, pp. 68-71.
M. E. Nikiforova, et al., "Unusual magnetic behavior of the new supramolecular ensemble [Ni$_2$L$_4$]2•[NiCl$_2$(LH)$_2$(MeCN)$_2$]•4MeCN (LH is 2-mercaptobenzimidazole)", Russian Chemical Bulletin, vol. 55, Issue 12, Dec. 2006, pp. 2181-2186 (Abstract only).
F. D. Rochon, et al., "Synthesis of aminoalcohol compounds of platinum and crystal structure of trans-[Pt(2-amino-2-methyl-1-propanol)$_2$Cl$_2$]", Canadian Journal of Chemistry, vol. 62, No. 12, May 28, 1984, pp. 2657-2660.
Sigeaki Fujieda, et al., "Synthesis and Antitumor Activity of Platinum Complexes with Cyclic Thioamides", The Japan Institute of Heterocyclic Chemistry, vol. 15, No. 2, 1981, pp. 743-746 (Abstract only).
Shuji Emori, et al., "Magnetic Properties of Diisothiocyanatobis(thiourea)nickel(II) and Related Complexes", Bulletin of the Chemical Society of Japan, vol. 44, No. 12, Dec. 1971, pp. 3299-3304.
C. Puglisi, et al., "Some substituted thiourea complexes of nickel (II) thiocyanate", Journal of Inorganic and Nuclear Chemistry, vol. 29, Issue 4. Apr. 1967, pp. 1069-1077 (Abstract only).

\* cited by examiner

*Primary Examiner* — Golam M Shameem
(74) *Attorney, Agent, or Firm* — Oblon, McClelland, Maier & Neustadt, L.L.P.

(57) ABSTRACT

The invention is directed to platinum(II) thione complexes of formula (I) and to methods of treating cancer using these complexes.

7 Claims, 9 Drawing Sheets

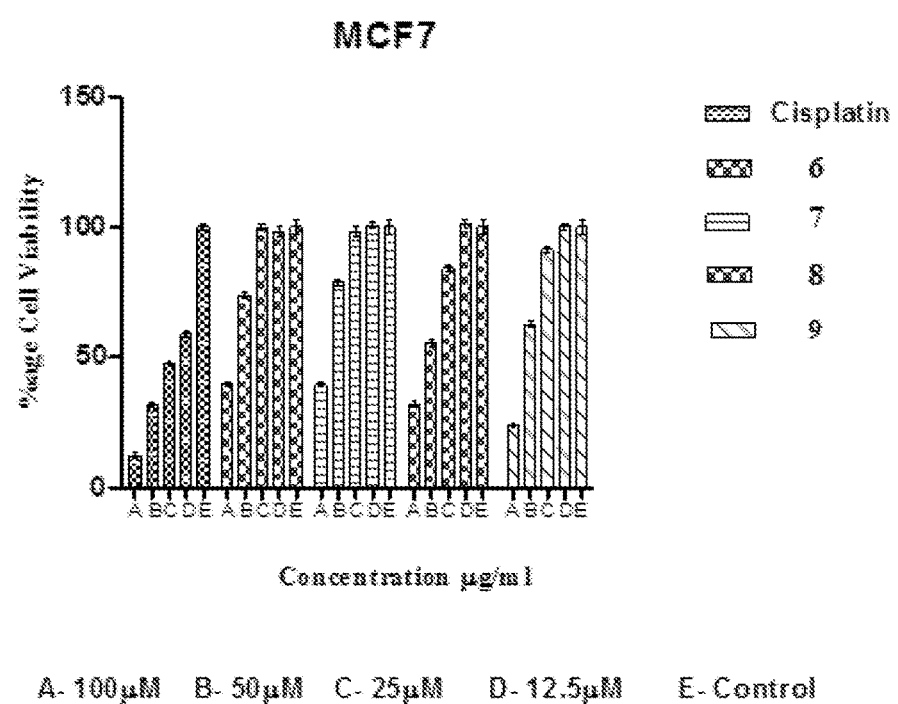

METHOD FOR INHIBITING CANCER CELL GROWTH WITH A TRANSPLATIN COMPLEX

CROSS-REFERENCE TO RELATED APPLICATIONS

The present application is a Continuation of Ser. No. 15/715,964, now allowed, having a filing date of Sep. 26, 2017.

BACKGROUND

Field of the Invention

The present disclosure relates to platinum(II) complexes of heterocyclic thiones with anti-cancer activity and to methods of treating cancer using these complexes.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Platinum anticancer compounds in clinical use such as, cisplatin, carboplatin and oxaliplatin generally exist as neutral molecules and contain two fairly labile cis ligands, e.g., the two chloro groups in cisplatin. The labile ligands are replaced by water through aquation reactions and the resulting cations form bifunctional adducts with DNA. See T. C. Johnstone, et al., Chem. Rev. 16 (2016) 3436-3486; N. J Wheate, et al., Dalton Trans. 39 (2010) 8113-8127; J. J. Wilson, et al., Chem. Rev. 14 (2014) 4470-4495; Y. Jung, et al., Chem. Rev. 107 (2007) 1387-1407; D. Wong, et al., Nature Rev. Drug Disc. 4 (2005) 307-320; L. Kelland. Nat Rev Cancer. 7 (2004) 573-584; S. Dasari, et al., Eur. J. Pharmacol. 2014, 364-378; S. V. Zutphen, et al., Coord. Chem. Rev. 249 (2005) 2845-2853; S. Ahmad, Chemistry & Biodiversity 7 (2010) 543-566; T. W. Hambley, J. Chem. Soc., Dalton Trans. 2711 (2001); E. R Jamieson, et al., Chemical Reviews. 99 (1999) 2467-2498; and S. Ahmad, et al., Tran Metal Chem. 31 (2006) 1003-1016, each incorporated herein by reference in their entirety. The platinum(II) complexes having two labile groups in a trans conformation, for example trans-[Pt(NH$_3$)$_2$Cl$_2$] (transplatin) or monofunctional platinum(II) complexes, such as [PtCl(dien)]Cl (dien=diethylenetriamine) or [Pt(NH$_3$)$_3$Cl]Cl were ineffective. See E. R Jamieson et al., Chemical Reviews. 99 (1999) 2467-2498; S. Ahmad, et al., Tran Metal Chem. 31 (2006) 1003-1016; and K. S Lovejoy, et al, Dalton Trans (2009) 10651-10659, each incorporated herein by reference in their entirety. But later studies have shown that the replacement of one (or both) amine ligand(s) of transplatin by aliphatic amines or heterocyclic ligands such as planar pyridine or non-planar piperazine greatly enhances the cytotoxicity of such species with respect to their corresponding cis isomers and also to cisplatin particularly, in cisplatin-resistant tumor cell lines. See J. Kasparkova, et al., J. Inorg. Biochem. 153 (2015) 206-210; J. M. Perez, et al., Crit. Rev. Oncol. Hematol. 35 (2000) 109-120; Natile, G., et al., Coord Chem Rev 216-217 (2001) 383-410; Y. Najajreh, et al., J. Med. Chem 45(2002) 5189-5195; S. M. Aris, et al., Eur. J. Inorg. Chem. (2009) 1293-1302; C. Bartel, et al., J. Biol. Inorg Chem. 17 (2012) 465-74; and A. G Quiroga. J. Inorg. Biochem 114 (2012) 106-112, each incorporated herein by reference in their entirety.

Like cis-platinum-amine complexes, DNA is also considered as the potential cellular target for the antitumor derivatives of transplatin. However, the nature of Pt-DNA adducts is different for the two types of complexes. Cisplatin and its analogues mainly form 1,2-intrastrand cross-links, while transplatin is not able to form 1,2-intrastrand cross-links, because of the steric hindrance of the two amine groups in trans position. Instead it mainly forms 1,3-interstrand cross-links. See, A. Eastman, et al., Biochemistry 26 (1987) 3303-3307, incorporated herein by reference in its entirety. Transplatin may form 1,3-intrastrand cross-links between two G residues, or between a G and a C residue, separated by at least one base. The enhancement of activities in trans complexes was connected mainly with their enhanced accumulation in tumor cells and efficiency to form in DNA a markedly higher amount of more distorting cross-links than transplatin, which forms in DNA preferentially less distorting and persisting monofunctional adducts.

Several structural studies of thione derivatives of transplatin have been reported, which describe a square-planar geometry around the metal center and the thione coordination in terminal S-bonded modes. See Arpalahti, et al., Inorg. Chim. Acta 153 (1988) 51-55; A. N. Westra, et al., Acta Crystallogr. C60 (2004) m395-m398; J. Fang, et al., Inorg Chim Acta 411 (2014) 5-10; Seerat-ur-Rehman, et al., Inorg Chem Commun, 36 (2013) 68-71; and S. Ahmad, et al., Monatsch. Chem. (2016), each incorporated herein by reference in their entirety. However, the antitumor properties of these complexes were not reported, although many other transplatin analogues are known to exhibit anticancer activities.

The inventors disclose herein the synthesis, spectroscopic investigation and determination of anticancer properties of the platinum(II) heterocyclic thione complexes disclosed herein.

These complexes have been characterized by elemental analysis, IR, and NMR ($^1$H & $^{13}$C) spectroscopy and their cytotoxic activity evaluated against several different types of cancer cells including the MCF7 (breast cancer), HCT15 (colon cancer) and A549 (lung carcinoma) cell lines.

BRIEF SUMMARY OF THE INVENTION

The invention is directed to platinum complexes of formula (I) and to methods of treating cancer using these complexes. Formula (1) is:

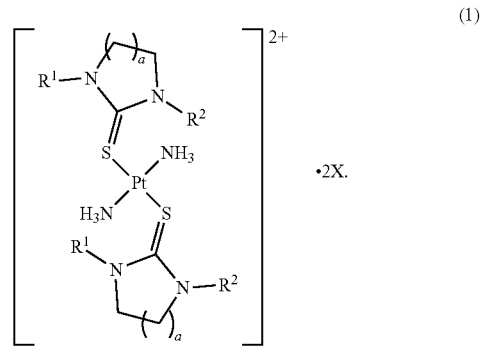

Preferably, in a compound having the core structure of Formula (1), each $R^1$ and $R^2$ is independently a hydrogen, a methyl group, an ethyl group, a propyl group, or an isopropyl group; a is 1, 2, or 3; and X is nitrate, fluoride, chloride, bromide, iodide, or acetate.

BRIEF DESCRIPTION OF THE DRAWINGS

FIGS. 6A and 6B show effects of concentrations of 100, 50, 25, 12.5 and 0 µM of Complexes 1 to 9 on MCF-7 cell viability. MCF-7 is a widely used epithelial cancer cell line derived from breast adenocarcinoma.

DETAILED DESCRIPTION OF THE INVENTION

Figure 1:
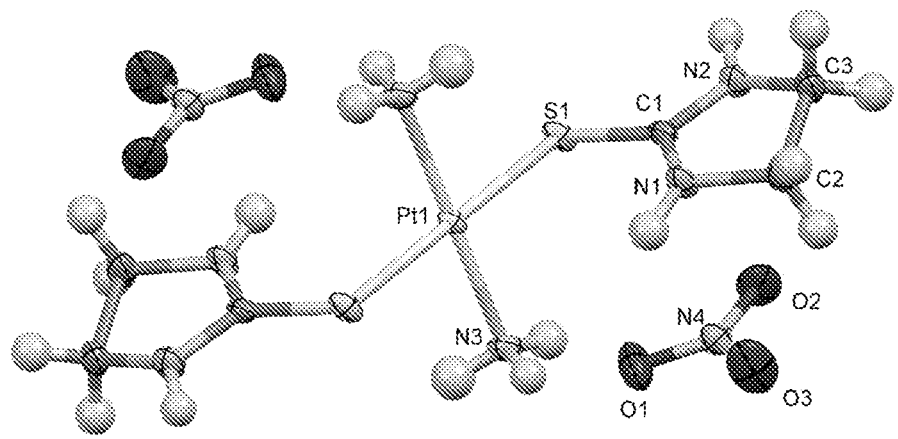
FIG. 1 provides a view of the molecular structure of Complex 1 with atomic labelling. The displacement ellipsoids are drawn at the 50% probability level. Atoms not labelled are related by inversion symmetry.

One aspect of the invention is directed to platinum(II) complexes of heterocyclic thiones (L) based on transplatin having the general formula, trans-[Pt(NH$_3$)$_2$(Thione)$_2$]·2NO$_3$. Another aspect of the invention is the use of these complexes as cytotoxic agents, especially against cancer cells.

The inventors have successfully synthesized and then characterized these complexes using elemental analysis, IR, and NMR ($^1$H & $^{13}$C) spectroscopy.

The crystal structures of two of them, trans-[Pt(NH$_3$)$_2$(Imt)$_2$]·2NO$_3$ (Complex 1) and trans-[Pt(NH$_3$)$_2$(Me$_2$Imt)$_2$]·2NO$_3$ (Complex 3) were determined by x-ray crystallography. The structures of Complexes 1 and 3 consist of trans-[Pt(NH$_3$)$_2$L$_2$]$^{2+}$ complex ions and nitrate counter ions. The platinum atom in both the complex ions adopts a distorted square planar geometry.

The spectroscopic data indicated the coordination of thione ligands to platinum(II).

The in vitro cytotoxicity of these compounds as well as of cisplatin and carboplatin was investigated using MTT assay against three human cancer cell lines, which were A549 (human lung carcinoma), MCF-7 (human breast carcinoma) and HTC15 (human colon cancer). The in vitro cytotoxicity's in several cases were comparable or even higher than cisplatin and carboplatin. Crystal structures of two of the complexes, trans-[Pt(NH$_3$)$_2$(Imt)$_2$]·2NO$_3$ (Complex 1) and trans-[Pt(NH$_3$)$_2$(Me$_2$Imt)$_2$]·2NO$_3$ (Complex 3) were also determined.

The present disclosure will be better understood with reference to the following definitions:

As used herein, "compound" and "complex" are used interchangeably, and are intended to refer to a chemical entity, whether in the solid, liquid or gaseous phase, and whether in a crude mixture or purified and isolated.

"Platinum(II) heterocyclic thione complex" according to the invention comprises the chemical formula trans-[Pt(NH$_3$)$_2$(Thione)$_2$]·[counterions]. Preferred counter ions for this complex are two nitrate (NO$_3$) groups.

The term "active ingredient", as used herein, refers to an ingredient in the composition that is biologically active, for example, the platinum(II) thione complex disclosed herein, a salt thereof, a prodrug thereof, or a solvate thereof.

Cytotaxic Activity.

In one embodiment, the IC$_{50}$ of the platinum(II) thione complexes is in a range of 0.01-200 µM, 0.1-100 µM, 1-100 µM, 10-90 µM, 20-80 µM, 30-80 µM, 40-80 µM, 50-80 µM, or 50-75 µM. These ranges include all intermediate subranges and values.

As used herein, the term "IC$_{50}$" refers to a concentration of a platinum(II) thione complex, the salt thereof, the prodrug thereof, or the solvate thereof, which causes the death of 50% of cancer or proliferating cells in 72 hours (3 days) such as the A549, MCF-7, or HTC15 cancer cell lines described herein. The IC$_{50}$ can be determined by standard cell viability assays, such as, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. Preferably, a MTT assay and/or a Trypan Blue assay is used.

Biormarkers.

Alternatively to use of IC$_{50}$ values, efficacy of treatment with a platinum(II) thione complex of the invention may be determined by measuring or detecting a change in one or cancer biomarkers, for example, comparing quantity of biomarkers in a blood or tissue sample before and after a treatment.

A treatment may significantly decrease the concentration of a particular biomarker, for example, by 5, 10, 15, 20, 25, 30, 35, 40, 45, 50, 55, 60, 65, 70, 75, 80, 85, 90, or 100%, compared to a control or pre-treatment value. As used herein, the term "biomarker" refers to a characteristic that is objectively measured and evaluated as an indicator of normal biological processes, pathogenic processes or pharmacological responses to a therapeutic intervention. Biomarkers include ER/PR, HER-2/neu for breast cancer, EGFR, KRAS, UGTIA1 for colorectal cancer, EML4/ALK, EGFR, and KRAS for lung cancer as well as other biomarkers described and incorporated by reference to https://_en.wikipedia.org/wiki/Cancer_biomarkers (last accessed Aug. 11, 2017). Cancer biomarkers are useful in determining the aggressiveness of an identified cancer as well as its likelihood of responding to the treatment. Examples of such prognostic biomarkers include, without limitation, CA125, β2-microglobulin, and EBV DNA. A change or mutation in a biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art. The concentration of the biomarker may be measured with an assay, for example an antibody-based method (e.g., an ELISA). As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like. Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences. The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor. In some embodiments, the concentration of the biomarker is measured before and after the administration. When the concentration of the biomarker is maintained, the method may further comprise increasing the effective amount of at least one of the platinum(II) thione complex of the invention, the salt thereof, the solvate thereof, the prodrug thereof, and the combination thereof by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount. In some embodiments, the mutation in the biomarker is detected before administrating the composition to identify subjects predisposed to the disease. For example, women with a BRCA1 germline mutation are at a higher risk of contracting ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

The term "counter-anion" refers to an anion, preferably a pharmaceutically acceptable anion, that is associated with a positively charged platinum(II) complex. Non-limiting examples of pharmaceutically counter-anions include nitrate, halides such as fluoride, chloride, bromide, iodide; nitrate; sulfate; phosphate; amide; methanesulfonate; ethanesulfonate; p-toluenesulfonate, salicylate, malate, maleate, succinate, tartrate; citrate; acetate; perchlorate; trifluoromethanesulfonate (triflate); acetylacetonate; hexafluorophosphate; and hexafluoroacetylacetonate. Use of $NO_3$ as a counterion makes the Pt(II) complex soluble in water, which is not possible for cisplatin or transplatin.

"Thiones" also known as thioketones or thiocarbonyls are organosulfur compounds related to conventional ketones. The thiones in the complexes of the invention are heterocyclic thiones. Preferred heterocyclic thiones include those having structures (a)-(g), (h) and (i):

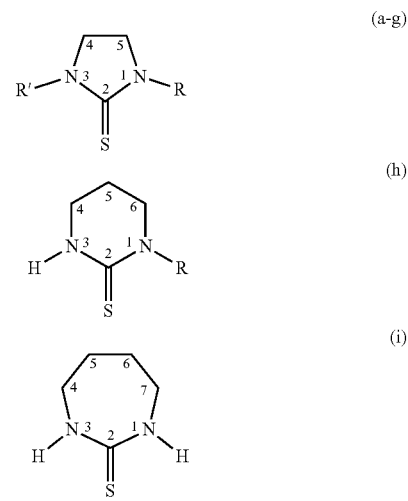

wherein thiones (a) through (i) comprise the following substituents:

(a) R=R' =H; Imidazolidine-2-thione (Imt),
(b) R=H, R' =$CH_3$; N-methylimidazolidine-2-thione (MeImt),
(c) R=$CH_3$, R' =$CH_3$; N,N'-dimethylimidazolidine-2-thione ($Me_2$Imt),
(d) R=R'=$C_2H_5$; N,N'-diethylimidazolidine-2-thione ($Et_2$Imt),
(e) R=H, R' =$C_3H_7$; N-propylimidazolidine-2-thione (PrImt),
(f) R=H, R'=i-$C_3H_7$; N-(isopropyl)imidazolidine-2-thione (i-PrImt),
(g) R=R'=i-$C_3H_7$; N,N'-(di-isopropyl)imidazolidine-2-thione ($iPr_2$Imt),
(h) R=$C_2H_5$; N-ethyl-1,3-Diazinane-2-thione (EtDiaz),
(i) 1,3-Diazepane-2-thione (Diap).

In some embodiments, other heterocyclic thiones, for example, those with only hydrogen on the nitrogen ring atoms, or those with other non-hydrogen substituents on the nitrogen or carbon ring atoms may also be used. In most embodiments, the thione rings in each complex are identical, however, some embodiments may contain different thione rings, for example, having different ring sizes or different substituents.

"Other substituents" that may appear on the heterothione rings include, but are not limited those defined below.

The term "alkyl", as used herein, unless otherwise specified, refers to a straight or branched hydrocarbon fragment such as a $C_1$-$C_6$ group. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, 1-methylcyclopropyl and 2-methylcyclopropyl groups, are included in the definition of cycloalkyl as used in the present disclosure. The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl. The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), IH-indolyl, isoquinolyl (or its N-oxide), or quinolyl (or its N-oxide), for example. As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined hereinafter); halogen (e.g. chlorine, bromine, fluorine or iodine); alkoxy (i.e. straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl); hydrocarbyl; arylalkyl; hydroxy; alkoxy; oxo; alkanoyl; alkanoyloxy; amino; alkylamino; arylamino; arylalkylamino; disubstituted amines (e.g. in which the two amino substituents are selected from the exemplary group including, but not limited to, alkyl, aryl, or arylalkyl); alkanoylamino; thiol; alkylthio; arylthio; arylalkylthio; alkylthiono; arylthiono; aryalkylthiono; alkylsulfonyl; arylsulfonyl; arylalkylsulfonyl; sulfonamido (e.g., —SO$_2$NH$_2$); substituted sulfonamide; nitro; cyano; carboxy; carbamyl (e.g., —CONH$_2$, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety). The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3, dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl. The term "alkylthio" as used in this disclosure refers to a divalent sulfur with alkyl occupying one of the valencies and includes the groups methylthio, ethylthio, propylthio, butylthio, pentylthio, hexylthio, and octylthio. The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl. Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring. The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl. The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl. "Vinyl" refers to an unsaturated substituent having at least one unsaturated double bond and having the formula CH2=CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl. The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

Compositions.

In most embodiments, the platinum(II) thione complex of the invention, the salt thereof, the solvate thereof, the prodrug thereof, or the combination thereof is formulated in a pharmaceutically acceptable composition. As used herein, a "composition" refers to a mixture of the active ingredient with other chemical components, such as pharmaceutically acceptable carriers and excipients. One purpose of a composition is to facilitate administration of the platinum(II) thione complex of the invention, the salt thereof, the solvate thereof, the prodrug thereof, or a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage. The phrase "pharmaceutically acceptable" as used herein refers to compounds, counterions, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo, ex vivo, or in vitro.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

Other Active Ingredients.

In some embodiments, other active ingredients in addition to the platinum(II) thione complex may be incorporated into a composition or separately administered in conjunction with a platinum(II) thione complex. In one embodiment, the composition is used for treating cancer and further comprises a second active ingredient, such as a chemotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder. Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-50 wt % of the second active ingredient, preferably 10-40 wt %, more preferably 10-20 wt %, relative to the weight of the first active ingredient.

Subjects.

The terms "patient", "subject", and "individual" are used interchangeably. As used herein, they refer to individuals suffering from a disease, at risk of further progression of a disease, or at risk of acquiring or developing the disease. None of the terms require that the individual be under the care and/or supervision of a medical professional.

These terms generally refer to humans, but also apply to mammals, avians and other animals especially domesticated or ecologically or commercially valuable animals. Mammals include non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In a preferred embodiment, the subject is a human.

A "subject in need of treatment" includes a subject already with the disease, a subject which does not yet experience or exhibit symptoms of the disease, and a subject predisposed to the disease. In preferred embodiments, the subject is a person who is predisposed to cancer, e.g. a person with a family history of cancer. In another embodiment, the subject refers to a cancer patient who has been previously administered/treated with cisplatin and have cisplatin resistance (for example in the form of high ERCC 1 mRNA levels, overexpression of HER-2/neu, activation of the PI3-K/Akt pathway, loss of p53 function, and/or over-expression of antiapoptotic bcl-2).

Cancers/Proliferative Disorders.

Cancers such as, but not limited to sarcomas, carcinomas, melanomas, myelomas, gliomas and lymphoma (including Hodkin lymphoma), can be treated or prevented with the platinum(IH) thione complexes provided herein.

In some embodiments, methods incorporating the use a platinum(II) thione complex of the present disclosure to treat or prevent cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system. In some embodiments, these methods are effective in the treatment or prevention of cervical, colon and lung cancers. Cancers or tumor resistant to other anticancer drugs, such as cisplatin-resistant cancers, may be treated. In treating certain cancers, the best approach is often a combination of surgery, radiotherapy, and/or chemotherapy. Therefore, in at least one embodiment, the composition is employed in conjunction with conventional radiotherapy and/or chemotherapy. In another embodiment, the composition is employed with surgery. The radiotherapy and/or surgery may be before or after the composition is administered.

Other non-cancerous proliferative diseases, disorders or conditions may also be treated, such as atherosclerosis, rheumatoid arthritis, psoriasis, idiopathic pulmonary fibrosis, scleroderma, cirrhosis of the liver, or benign proliferative conditions such as verruca (warts), dermatitis, or other disorders characterized by epidermal cell proliferation.

Therapy.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

Administration.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection including intravenous, subcutaneous, intraperitoneal, intramuscular, intravascular, or infusion, topical and rectal administration. Those of ordinary skill in the art are familiar with administration techniques that can be employed with the compounds and methods described herein. In preferred embodiments, the active ingredient and/or the composition described herein are administered orally.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the platinum(H) thione complex of the invention, the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, or tolerance and resistance of the body to the administered drug, and then determined and adjusted accordingly. In at least one embodiment, the at least one of the platinum (II) thione complex of the invention, the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg.

In some embodiments, a treatment will involve administering a composition comprising at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the platinum(II) thione complex of the invention. The composition may comprise 0.01-50 µM, 0.01-30 µM, preferably 0.01-10 µM of the platinum(II) thione complex of the invention relative to the total composition. In some embodiments, the composition comprises up to 0.1 wt %, 1 wt %, 5 wt %, or 10 wt % of the pharmaceutically acceptable salt of the platinum(II) thione complex of the invention. In some embodiments, the composition comprises up to 0.1 wt %, 1 wt %, 5 wt %, or 10 wt % of the pharmaceutically acceptable solvate thereof of either the platinum(II) thione complex of the invention. These ranges include all intermediate subranges and values.

A treatment method may comprise administering a composition containing the platinum(II) thione complex of the invention as a single dose or multiple individual divided doses. In some embodiments, the composition is administered at various dosages (e.g., a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

EMBODIMENTS

The following examples illustrate various aspects of the present invention. They are not to be construed to limit the claims in any manner whatsoever. Nonlimiting embodiments of the invention include a method for inhibiting cell growth, proliferation, or viability by contacting a cell or tissue with a platinum(II) thione complex according to the invention, such as that depicted by Formula (1):

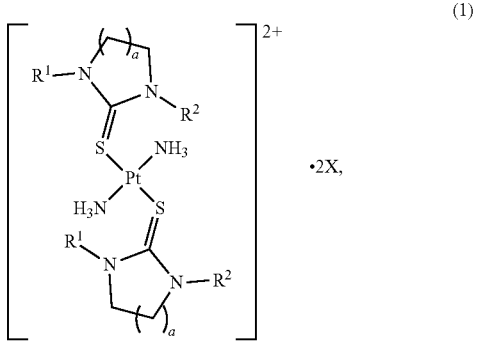

wherein $R^1$ and $R^2$ are each, independently, a hydrogen or a $C_1$-$C_6$ alkyl group, a is 1, 2 or 3; and X is nitrate, fluoride, chloride, bromide, iodide, or acetate. This method may be practiced by administering at least one of Complexes 1, 2, 3, 4, 5, 6, 7, 8 or 9. One or more platinum(II) thione complexes of the invention may be administered to a subject in need of inhibition of cellular proliferation, such as inhibition of growth of tumor, cancerous, or neoplastic tissue or inhibition of benign hyperplasias. Exemplary subjects for treatment include those with breast, colon or lung cancer. The platinum(II) thione complexes of the invention may be administered based on the nature of the subject treated and disease or disorder treatment. For example, they may be administered orally, parenterally, including intradermally, intramuscularly, intravenously, rectally, or by inhalation, topically or by other known modes of administration. They may be administered directly into a tumor or into a site infiltrated by cancer cells. In some embodiments the platinum(II) thione complex is administered along with a radiation treatment, surgical treatment, and/or another chemotherapeutic treatment.

Another aspect of the invention is directed to a platinum (II) thione complex represented by Formula (1):

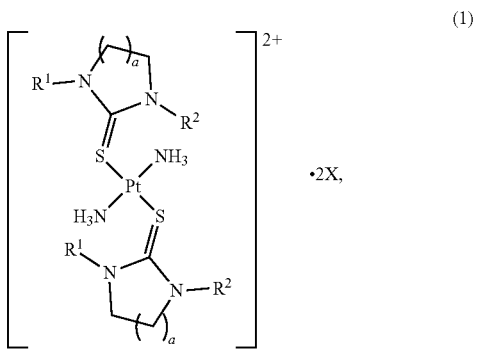

wherein $R^1$ and $R^2$ are each, independently, a hydrogen or a $C_1$-$C_6$ alkyl group, a is 1, 2 or 3; and X is nitrate, fluoride, chloride, bromide, iodide, or acetate. Specific embodiments of this complex include those where a is one and the thione rings have 5 ring atoms, where a is two and the thione rings have six ring atoms, or where a is three and the thione rings have seven ring atoms. Specific and exemplified embodiments of this complex are described by Complexes 1 to 9. In some embodiments, one of more of the $R^1$ or $R^2$ is not hydrogen, for example, when a is 2 or 3, at least one of $R^1$ or $R^2$ may be $C_1$-$C_6$ alkyl and/or X is nitrate.

Example 1

Synthesis of Platinum(II) Thione Complexes

Transplatin (trans-diamminedichloidoplatinum(II)) was obtained from Strem Chemical Company, USA. Dimethylsulfoxide-$d_6$ and $D_2O$ were purchased from Fluka Chemical Co. The thione ligands were prepared according to the procedure mentioned in the literature [27, 28]. (3-(4,5-Dimethylthiazol-2-yl)-2,5-diphenyltetrazolium bromide, a yellow tetrazole) was purchased from Sigma Chemical Co, St. Louis, Mo., USA.

Trans-[Pt(NH$_3$)$_2$(Imt)$_2$].2NO$_3$ c Complex 1 through Complex 9 were synthesized using the following general steps. All the compounds were prepared by adding (0.17 g, 1.0 mmol) of AgNO$_3$ to the solutions containing (0.15 g, 0.5 mmol) of trans-diamminedichloridoplatinum(II) (transplatin) in 10 mL water and stirring the mixture for 2 hours in the dark at room temperature. The solution was filtered to remove silver chloride as solid. Then 1.0 mmol of thione ligand dissolved in 10 mL methanol were added to the filtrates drop wise. Mixing and stirring of the solutions resulted in a colored solution. The solution was filtered and kept at room temperature. Solid powder was obtained on slow evaporation of the solvent. The complexes, trans-[Pt(NH$_3$)$_2$(Imt)$_2$](NO$_3$)$_2$ and trans-[Pt(NH)(Me$_2$Imt)$_2$](NO$_3$)$_2$ were crystallized from a 1:1 mixture of water and methanol. Purity of the product was assessed through elemental analysis of C, H, N, and S. The CHNS data, melting/decomposition points, and % yield of the synthesized complexes are presented below:

Complex 1. trans-[Pt(NH$_3$)$_2$(Imt)$_2$]. 2NO$_3$: M. p. 156-158° C., Yield was: 0.256 g, 92%. C, H, N, and S % [Calculated C: 12.93%, H: 3.25%, N: 20.10, S: 11.50%, Found: C: 12.23%, H: 3.28%, N: 20.89%, S: 11.75%]. IR: $v_{max}$=3310 (s), 1042 (s), 501 (s), 836 (s), 272 (s).

Complex 2. trans-[Pt(NH$_3$)$_2$(MeImt)$_2$]. 2NO$_3$: M.p. 140-142° C., Yield was: 0.234 g, 80%. C, H, N, and S % [Calculated C: 16.41%, H: 3.79%, N: 19.14, S: 10.95%, Found: C: 16.28%, H: 3.63%, N: 19.52%, S: 10.76%]. IR: $v_{max}$=3528 (s), 1112 (s), 837 (s), 503 (s), 274 (s).

Complex 3. trans-[Pt(NH$_3$)$_2$(Me$_2$Imt)$_2$]. 2NO$_3$: M.p. 130-132° C., Yield was: 0.2488, 81%. C, H, N, and S % [Calculated C: 19.57%, H: 4.27%, N: 18.16, S: 10.45%, Found: C: 19.22%, H: 4.25%, N: 18.87%, S: 10.57%]. IR: $v_{max}$=1118 (s), 825 (s), 491 (s), 265 (s).

Complex 4. trans-[Pt(NH$_3$)$_2$(Et$_2$Imt)$_2$]. 2NO$_3$: M.p. 124-126° C., Yield: 0.224 g, 67%. C, H, N, and S %. [Calculated C: 25.11%, H: 5.12%, N: 16.73, S: 9.58%, Found: C: 25.38%, H: 5.23%, N: 16.75%, S: 9.72%]. IR: $v_{max}$=1065 (s), 826 (s), 502 (s), 284 (s).

Complex 5. trans-[Pt(NH$_3$)$_2$(PrImt)$_2$]. 2NO$_3$: M.p. 106-108° C., Yield was: 0.247 g, 77%. C, H, N, and S % [Calculated C: 22.46%, H: 4.71%, N: 17.48, S: 9.99%, Found: C: 22.87%, H: 4.83%, N: 17.21%, S: 10.05%]. IR: $v_{max}$=3373 (s), 1033 (s), 824 (s), 503 (s), 282 (s).

Complex 6. trans-[Pt(NH$_3$)$_2$(iPrImt)$_2$]. 2NO$_3$: M. p. 83-85° C., Yield was: 0.234 g, 73%. C, H, N, and S % [calculated C: 22.46%, H: 4.71%, N: 17.48, S: 9.99%, Found: C: 21.98%, H: 4.49%, N: 17.38%, S: 9.48%]. IR: $v_{max}$=3566 (s), 1064 (s), 867 (s), 495 (s), 279 (s).

Complex 7. trans-[Pt(NH$_3$)$_2$(Pr$_2$Imt)$_2$].2 NO$_3$: M. p. 132-134° C., Yield was: 0.210 g, 58%. C, H, N, and S % [Calculated C: 29.79%, H: 5.83%, N: 15.44, S: 8.84%, Found: C: 29.89%, H: 5.87%, N: 15.27%, S: 8.58%]. IR: $v_{max}$=1106 (s), 856 (s), 497 (s), 283 (s).

Complex 8. trans-[Pt(NH$_3$)$_2$(EtDiaz)$_2$]. 2NO$_3$: M. p. 92-94° C., Yield was: 0.227g, 71%. C, H, N, and S % [Calculated C: 22.46%, H: 4.71%, N: 17.48, S: 9.99%, Found: C: 22.25%, H: 4.68%, N: 17.37%, S: 9.78%]. IR: $v_{max}$=3448 (s), 1074 (s), 835 (s), 501 (s), 279 (s).

Complex 9. trans-[Pt(NH$_3$)$_2$(Diap)$_2$]. 2NO$_3$: M. p. 164-166° C., Yield was: 0.191 g 62%. C, H, N, and S % [Calculated C: 19.57%, H: 4.27%, N: 18.26, S: 10.45%, Found: C: 19.72%, H: 4.32%, N: 18.07%, S: 10.33%]. IR: $v_{max}$=3270 (s), 1053 (s), 822 (s), 510 (s), 269 (s).

The nitrate derivatives of transplatin were first prepared by addition of two equivalents of AgNO$_3$ to transplatin. The nitrate species were then reacted with thione ligands in a 1:2 molar ratio to produce the complexes of the general formula, trans-[Pt(NH$_3$)$_2$(L)$_2$].2NO$_3$. The elemental analysis data is consistent with this composition.

Example 2

Spectroscopic Measurements

Elemental analysis of was performed on Perkin Elmer Series 11 (CHNS/O), Analyzer 2400. The solid state FTIR spectra of the ligands and their platinum(II) complexes were recorded on a Perkin Elmer FTIR180 spectrophotometer or NICOLET 6700 FTIR using KBr pellets over the range 4,000-400 cm$^{-1}$.

The $^1$H and $^{13}$C NMR spectra in DMSO were carried out on a JEOL JNM-LA 500 NMR spectrometer at 500.00 MHz and 125.65 MHz operating frequency respectively. The $^{13}$C NMR spectra were recorded with $^1$H broadband decoupling at 297 K. The spectral conditions were; 32 K data points, 0.963 s acquisition time, 3.2 s pulse delay and a 5.75 µs pulse width for $^1$H NMR, and 32 K data points, 0.963 s acquisition time, 2.5 s pulse delay and a 5.12 µs pulse width for $^{13}$C NMR. The chemical shifts were measured relative to Tetramethylsilane (TMS).

Example 3

X-Ray Diffraction Analysis

The intensity data for Complex 1 and (3) were collected at 173K (−100° C.) on a Stoe Mark II-Image Plate Diffraction System. See Stoe & Cie. X-Area & X-RED32. Stoe & Cie GmbH, Darmstadt, Germany. (2009), incorporated herein by reference in its entirety. Equipped with a two-circle goniometer and using MoKα graphite monochromated radiation (λ=0.71073 Å). The structure was solved by direct methods with SHELXS-97. See G. M. Sheldrick. Acta Cryst. A64 (2008)112-122, incorporated herein by reference in its entirety. The refinement and all further calculations were carried with SHELXL-2014. See G. M. Sheldrick. Acta Cryst. C71 (2015) 3-8, incorporated herein by reference in its entirety.

The N- and C-bound H-atoms were included in calculated positions and treated as riding atoms with N—H=0.91 Å, C—H=0.99 and 0.98 Å for CH$_2$ and CH$_3$ H-atoms, respectively, and with U$_{iso}$(H)=1.5 U$_{eq}$(C) for methyl H atoms and =1.2 U$_{eq}$ (N or C) for other H atoms. The non-H atoms were refined anisotropically, using weighted full-matrix least-squares on F$^2$. A semi-empirical absorption correction was applied using the MULABS routine in PLATON. See A. L. Spek. Acta Cryst. D65(2009) 148-155, incorporated herein by reference in its entirety. A summary of crystal data and refinement details for Complexes 1 and 3 are given in Table 1.

TABLE 1

Crystal data and refinement details for crystal structures of Complexes 1 and 3.

| Parameter | Complex 1 | (3) |
| --- | --- | --- |
| Formula | C$_6$H$_{18}$N$_6$PtS$_2$•2(NO$_3$) | C$_{10}$H$_{26}$N$_6$PtS$_2$•2(NO$_3$) |
| Formula weight | 557.49 | 613.60 |
| Crystal size/nun | 0.41 × 0.34 × 0.21 | 0.40 × 0.36 × 0.28 |
| Wavelength/Å | 0.71073 | 0.71073 |
| Temperature/K | 173 | 173 |
| Crystal symmetry | Monoclinic | Monoclinic |
| Space group | P 2$_1$/n | P 2$_1$/n |
| a/Å | 5.4002 (4) | 7.0160 (5) |
| b/Å | 23.4438 (15) | 18.6235 (10) |
| c/Å | 6.6485 (5) | 8.0794 (6) |
| β/° | 105.458 (6) | 107.228 (6) |
| V/Å$^3$ | 811.26 (10) | 1008.31 (12) |
| Z | 2 | 2 |
| ρ$_{calc}$/Mgm$^{-3}$ | 2.282 | 2.021 |
| µ(Mo—Kα)/mm$^{-1}$ | 8.95 | 7.21 |
| F(000) | 536 | 600 |
| θ value(°) | θ$_{max}$ = 25.6, θ$_{min}$ = 1.7 | θ$_{max}$ = 25.7, θ$_{min}$ = 2.2 |
| No. measured, independent and observed [I > 2σ(I)] reflections | 10466, 1532, 1332 | 13070, 1900, 1550 |
| R$_{int}$ | 0.087 | 0.046 |
| R[F$^2$ > 2σ(F$^2$)], wR(F$^2$), S | 0.023, 0.050, 1.04 | 0.015, 0.035, 0.98 |
| T$_{min}$, T$_{max}$ | 0.297, 1.000 | 0.402, 1.000 |
| Largest diff. peak, hole/Å$^{-3}$ | 0.99, −1.86 | 0.76, −0.75 |

Figure 2:
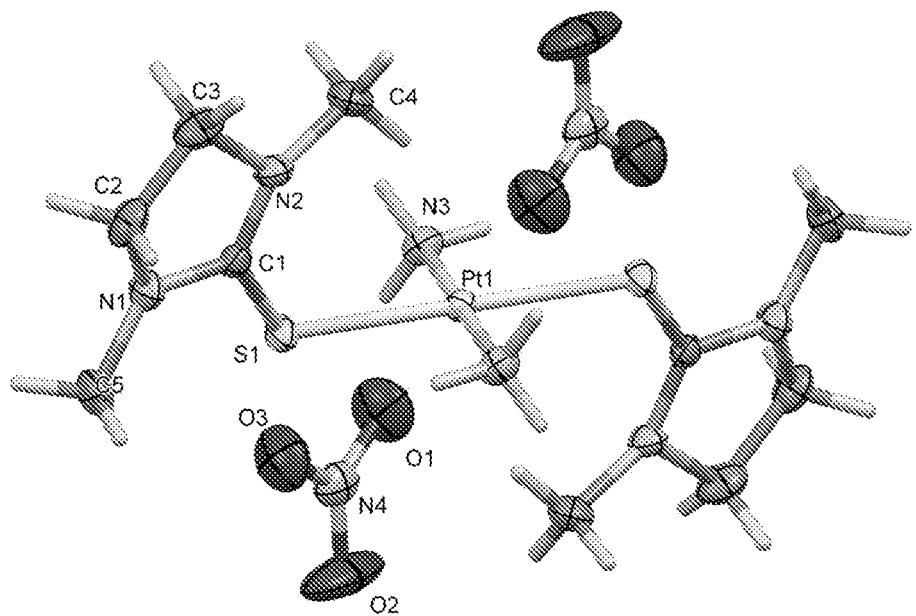
FIG. 2 provides a view of the molecular structure of Complex 3 with atomic labelling. The displacement ellipsoids are drawn at the 50% probability level. Atoms not labelled are related by inversion symmetry.

The molecular structures of Complexes 1 and 3 are shown in FIGS. 1 and 2 respectively. The selected geometrical parameters are given in Table 3. The structure of both complexes consists of a complex cation, [Pt(NH$_3$)$_2$(Imt)$_2$]$^{2+}$ in Complex 1 or [Pt(NH$_3$)$_2$(Me$_2$Imt)$_2$]$^{2+}$ in (2) and two nitrate ions. In the complex ions, Pt(II) atom is bound to two sulfur atoms of thione ligands and two N atoms of ammonia in a trans fashion. The platinum atom is located on the inversion center and adopts essentially a square-planar environment lying exactly within the plane defined by the two S and two N atoms. The cis angles around platinum vary between 87.50 (9°) and 92.50 (9°) in Complex 1, while in Complex 2 they are 88.52 (7)° and 91.48 (7)°. The trans angles in both are 180°. The Pt—N and Pt—S bond distances are 2.046 (3) and 2.3260 (9) Å in Complex 1 and, 2.054 (2) and 2.3199 (7) Å in Complex 2. These bond distance values are very close with the average bond distance values reported for similar complexes. See A. Z. A. Mustafa, et al., Inorg. Chem. Commu. 44 (2014) 159-163; A. Z. A.

Mustafa, et al., J. Coord. Chem. 68 (2015) 3511-3524; J. Lin, et al., J. Coord. Chem 61 (2008) 2457-2469; and M. E O'Neill, et al., (1982) Inorg Chim Acta 66: 79-84, each incorporated herein by reference in their entirety.

Figure 3:
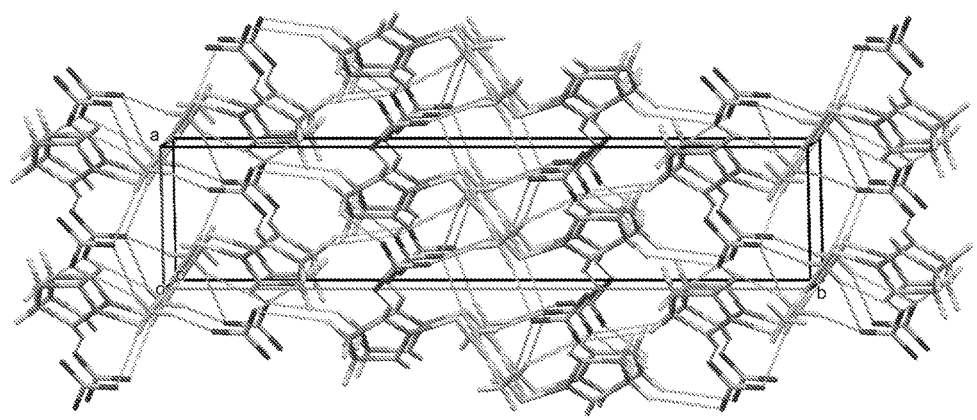
FIG. 3 shows the crystal packing of Complex 1, viewed along the c axis. The N—H . . . O, N—H . . . N and C—H . . . O hydrogen bonds are shown as dashed lines and lead to the formation of a three-dimensional structure.
Figure 4:
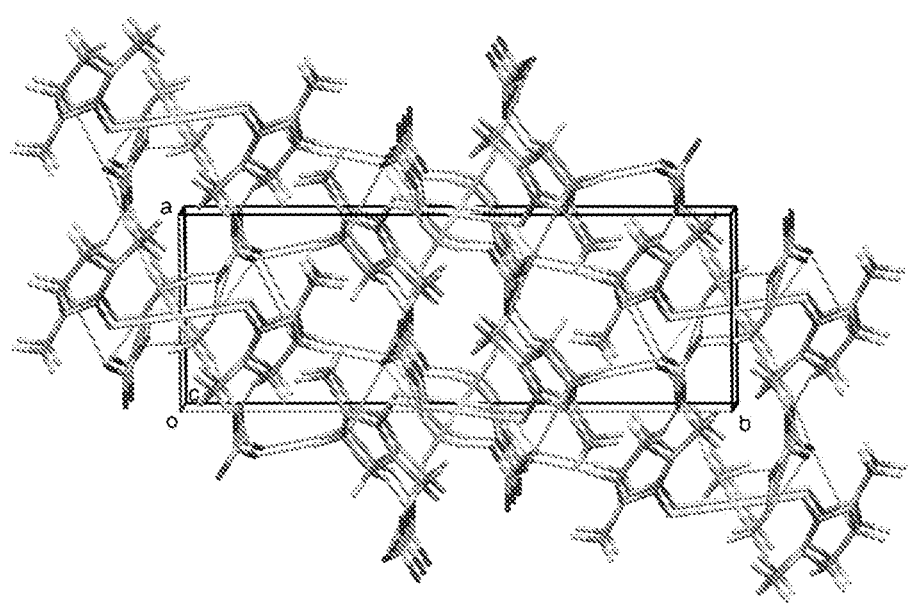
FIG. 4 show the crystal packing of Complex 3, viewed along the c axis. The N—H . . . O, N—H . . . N and C—H . . . O hydrogen bonds are shown as dashed lines and lead to the formation of a three-dimensional structure.

The complex cations, trans-[Pt(NH$_3$)$_2$(Thione)$_2$]$^{2+}$ and nitrate anions are associated to each other through formation of hydrogen bonds. In the crystal packing of complexes, the molecules are H-bonded via N—H of ammonia or C—H hydrogen of Imt and oxygen atoms of nitrate ion. In Complex 1, N—H hydrogen of Imt and in Complex 3, nitrogen atoms of NO$_3^-$ are also involved in hydrogen bonding. The nitrate anion nitrogen shows the weakest contact. The hydrogen bonding interactions result in the formation of three-dimensional hydrogen bonded network as shown in FIGS. 3 and 4 for Complex 1 and Complex 3 respectively.

TABLE 2

Selected bond distances (Å) and bond angles (°) for 1 and 3

| Bond Distance | | Bond angles | |
|---|---|---|---|
| Complex 1 | | | |
| Pt1—N3 | 2.046 (3) | N3—Pt1—S1 | 92.50 (9) |
| Pt1—S1 | 2.3260 (9) | N3$^i$—Pt1—S1 | 87.50 (9) |
| | | N3$^i$—Pt1—N3 | 180 |
| | | S1—Pt1—S1$^i$ | 180 |
| Complex 3 | | | |
| Pt1—N3 | 2.054 (2) | N3—Pt1—S1 | 88.52 (7) |
| Pt1—S1 | 2.3199 (7) | N3$^i$—Pt1—S1 | 91.48 (7) |
| | | N3$^i$—Pt1—N3 | 180 |
| | | S1—Pt1—S1$^i$ | 180 |

Symmetry codes: for 1, (i) −x, −y, −z + 1; for 3, (i) −x + 1, −y, −z + 1.

The crystal structures of two complexes revealed a distorted square planar geometry around platinum and the spectroscopic and crystallographic data strongly suggest that the thione ligands are coordinated to the Pt(II) center through the sulfur atom.

CCDC deposit numbers 1545440 and 1545441 refer to Complex 1 and Complex 3 respectively. Crystallographic data in CIF or other electronic format is incorporated by reference and can be obtained free of charge via www.ccdc.cam.ac.uk/data_request/cif, by e-mailing data_request@ccdc.cam.ac.uk, or by contacting the Cambridge Crystallographic Data Centre, 12 Union Road, Cambridge CB2 1EZ, UK; fax: +44(0)1223-336033.

Example 4

IR Spectroscopy

Selected IR frequencies of free thiones and their platinum (II) compounds are given in synthesis section. The characteristic vibrational bands in the IR spectra of thione complexes, are usually observed in three frequency regions; ν(C=S) vibration around 1200 and 600 cm$^{-1}$, the N—H stretching near 3200 cm$^{-1}$ and M-sulfur stretching band below 400 cm$^{-1}$. The presence of ν(N—H) and ν(C=S) bands in all complexes proves that the thione ligands are coordinated to the metal atom. The spectra of free ligands display a band around 600 cm$^{-1}$ as well as 1200 cm$^{-1}$ that belong to ν(C=S) stretching. See S. Ahmad, et al., Can. J. Chem. 80 (2002) 1279-1284; A. A. Isab, et al., Polyhedron. 21 (2002) 1267-1271; and B. P. Kennedy et al., Can. J. Chem. 50 (1972) 3488-3507, each incorporated herein by reference in their entirety. These bands shifted toward lower wave number upon complexation, while the N—H stretching vibrations shifted to higher frequency indicating the coordination of thiones through sulfur atom. In order to investigate the metal-sulfur stretching frequencies of the synthesized complexes, the spectra were recorded in far-infrared region below 400 cm$^{-1}$. This band lies in the range of about 300 cm$^{-1}$ for the transition-metal complexes according to the literature. See D. M. Adam et al., J. Chem. Soc. (1967) 884-889, incorporated herein by reference in its entirety. In all complexes, we observed a sharp peak around 280 cm$^{-1}$ that was assigned to platinum-sulfur bond. A sharp band around 825 cm$^{-1}$ for all trans-[Pt(NH$_3$)$_2$(L)$_2$].2NO$_3$ complexes and its absence in the free ligand spectra is attributed to the presence of non-coordinated nitrate ion.

Example 5

$^1$H and $^{13}$C NMR Spectroscopy

The $^1$H and $^{13}$C chemical shifts of the ligands and their platinum(II) complexes in DMSO-d$_6$ are given in Tables 5 and 6 respectively. In $^1$H NMR spectra of the complexes, the N—H signal of thiones became less intense upon coordination and shifted downfield from their positions in free ligands. The deshielding is related to an increase in υ electron density in the C—N bond upon coordination.

TABLE 3

$^1$H NMR chemical shifts (ppm) of thiones and their Pt(II) complexes in DMSO

| Species | N—H | H-4 | H-5 | H-6 | H-7/N—C3 | N—C1 | N—C2 |
|---|---|---|---|---|---|---|---|
| Imt | 7.90 | s, 4H, 3.59 | s, 4H, 3.59 | — | — | — | — |
| 1 | 9.09 | s, 4H, 3.69 | s, 4H, 3.69 | — | — | — | — |
| MeImt | 7.93 | t, 2H, 3.63 | t, 2H, 3.43 | — | — | s, 3H, 2.92 | — |
| 2 | 8.47 | t, 2H, 3.71 | t, 2H, 3.56 | — | — | s, 3H, 2.96 | — |
| Me$_2$Imt | — | s, 4H, 3.48 | s, 4H, 3.48 | — | — | s, 6H, 2.91 | — |
| 3 | — | s, 4H, 3.65 | s, 4H, 3.65 | — | — | s, 6H, 3.29 | — |
| Et$_2$Imt | — | s, 4H, 3.48 | s, 4H, 3.48 | — | — | q, 4H, 3.37 | t, 6H, 0.97 |
| 4 | — | s, 4H, 3.53 | s, 4H, 3.53 | — | — | q, 4H, 3.48 | t, 6H, 1.12 |
| PrImt | 7.99 | t, 2H, 3.58 | t, 2H, 3.41 | — | t, 3H, 0.73 | t, 2H, 3.31 | m, 2H, 1.45 |
| 5 | 8.81 | t, 2H, 3.76 | t, 2H, 3.62 | — | t, 3H, 0.79 | t, 2H, 3.35 | m, 2H, 1.55 |
| iPrImt | 7.96 | t, 2H, 3.53 | t, 2H, 3.38 | — | — | m, 1H, 4.35 | d, 6H, 1.00 |
| 6 | 8.31 | t, 2H, 3.70 | t, 2H, 3.54 | — | — | m, 1H, 4.25 | d, 6H, 1.07 |
| iPr$_2$Imt | — | s, 4H, 3.22 | s, 4H, 3.22 | — | — | m, 1H, 4.48 | d, 6H, 0.99 |
| 7 | — | s, 4H, 3.49 | s, 4H, 3.49 | — | — | m, 1H, 5.10 | d, 6H, 1.05 |
| EtDiaz | 7.89 | t, 2H, 3.62 | m, 2H, 1.83 | t, 2H, 3.28 | — | q, 2H, 3.12 | t, 3H, 1.02 |
| 8 | 8.65 | t, 2H, 3.59 | m, 2H, 1.84 | t, 2H, 3.33 | — | q, 2H, 3.21 | t, 3H, 1.09 |
| Diap | 7.70 | t, 4H, 1.67 | t, 4H, 3.18 | t, 4H, 3.18 | t, 4H, 1.67 | — | — |
| 9 | 8.70 | t, 4H, 1.70 | t, 4H, 3.24 | t, 4H, 3.24 | t, 4H, 1.70 | — | — | s: singlet, d: doublet, t: triplet, q: quartet, m: multiplet.

In $^{13}$C NMR, the C=S resonance of thiones in the complexes is shifted upfield by about 5.5-13.6 ppm as compared to that in free ligands in accordance with the data observed for other complexes of d$^{10}$ metals with thiones. The upfield shift is attributed to the lowering of C=S bond order upon coordination and a shift of N→C electron density, producing a partial double bond character in the C—N bond. As the shift difference of the C=S resonance may be related to the strength of metal-sulfur bond, Table 6 shows that the $Me_2Imt$ complex would be the most stable among these complexes. A small deshielding effect is observed in other carbon atoms, which is due to an increase in x character of the C—N bond.

Figure 5A:
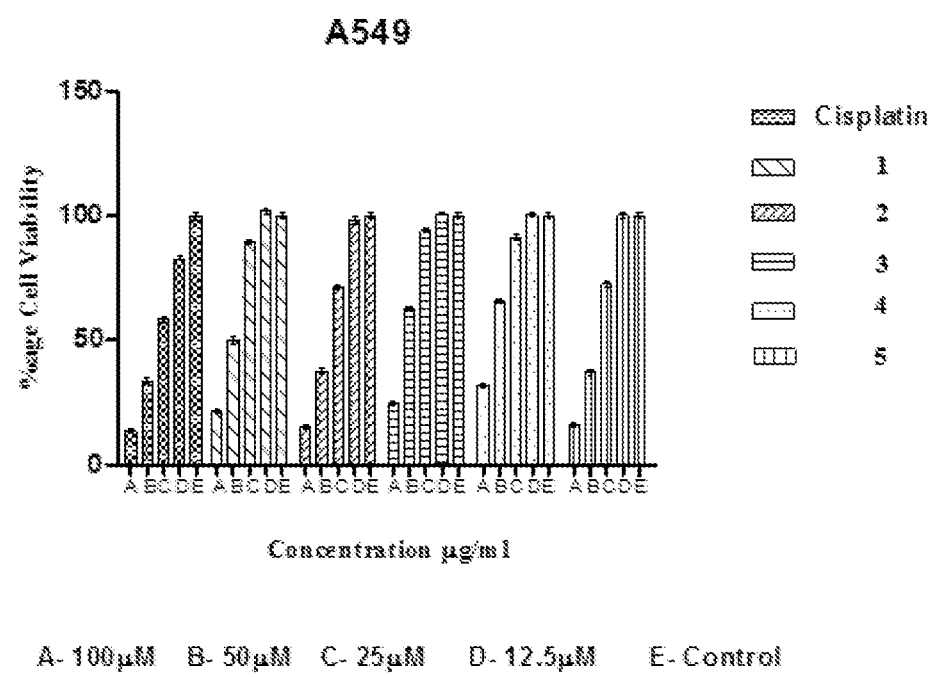
FIGS. 5A and 5B show effects of concentrations of 100, 50, 25, 12.5 and 0 µM of Complexes 1 to 9 on A-549 cell viability. A-549 is a widely used adenocarcinomic human alveolar basal epithelial cell line.
Figure 5B:
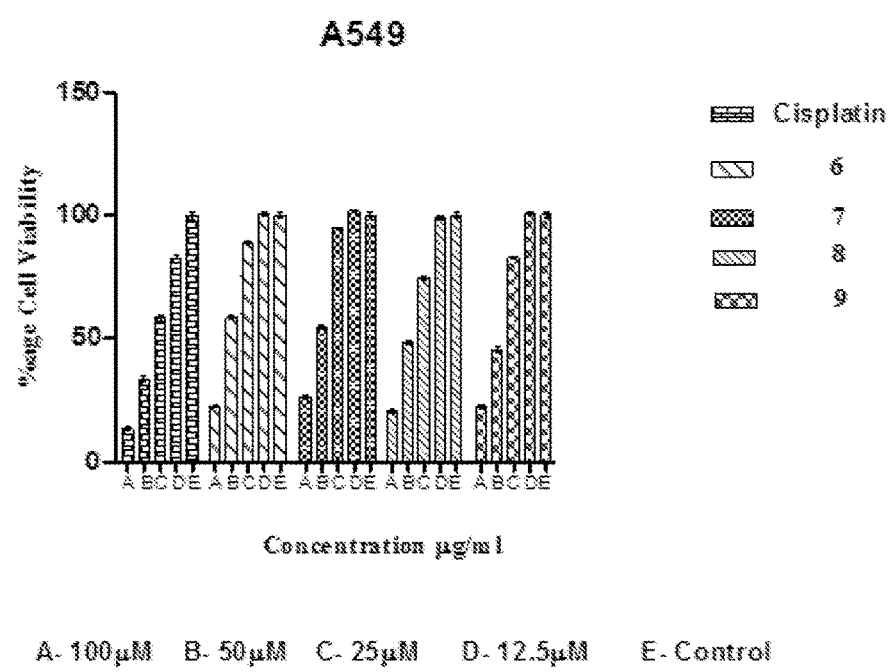
Figure 6A:
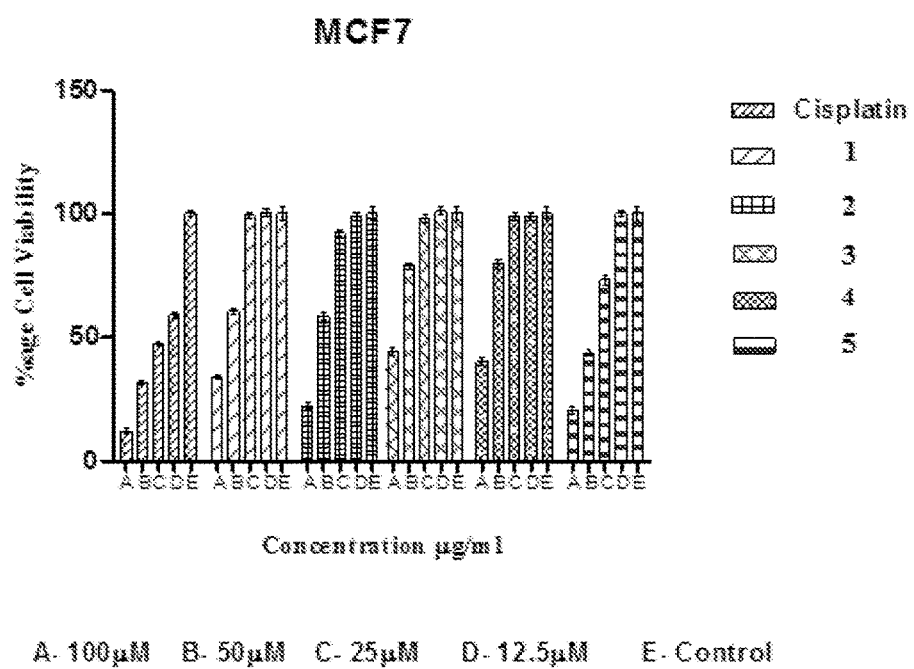
Figure 7A:
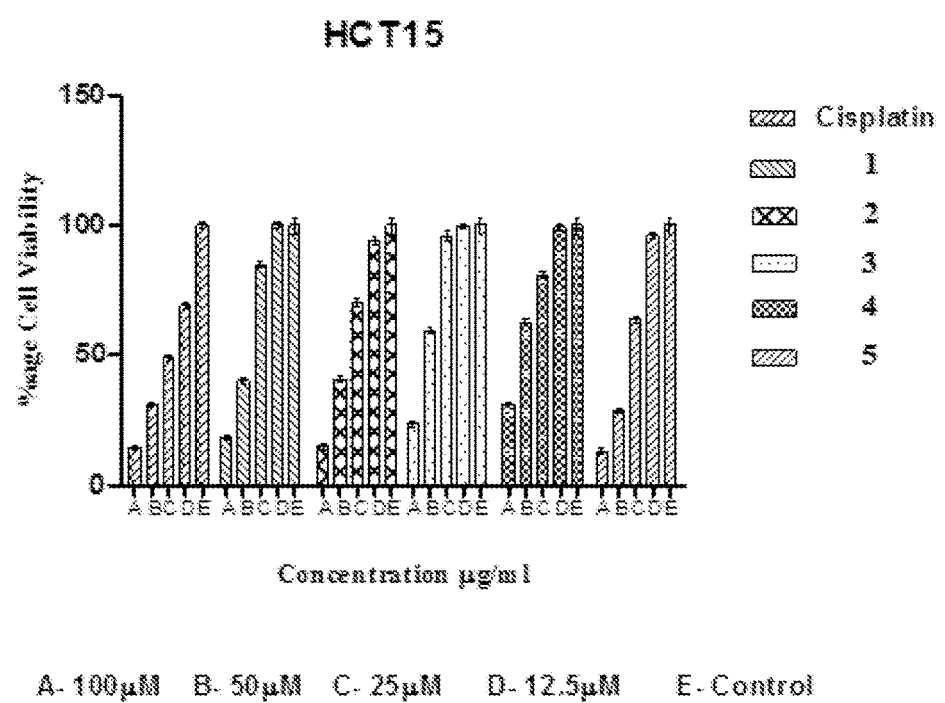
FIGS. 7A and 7B show effects of concentrations of 100, 50, 25, 12.5 and 0 µM of Complexes 1 to 9 on HCT-15 cell viability. HCT-15 is a widely used colon cancer cell line derived from colon adenocarcinoma.
Figure 7B:
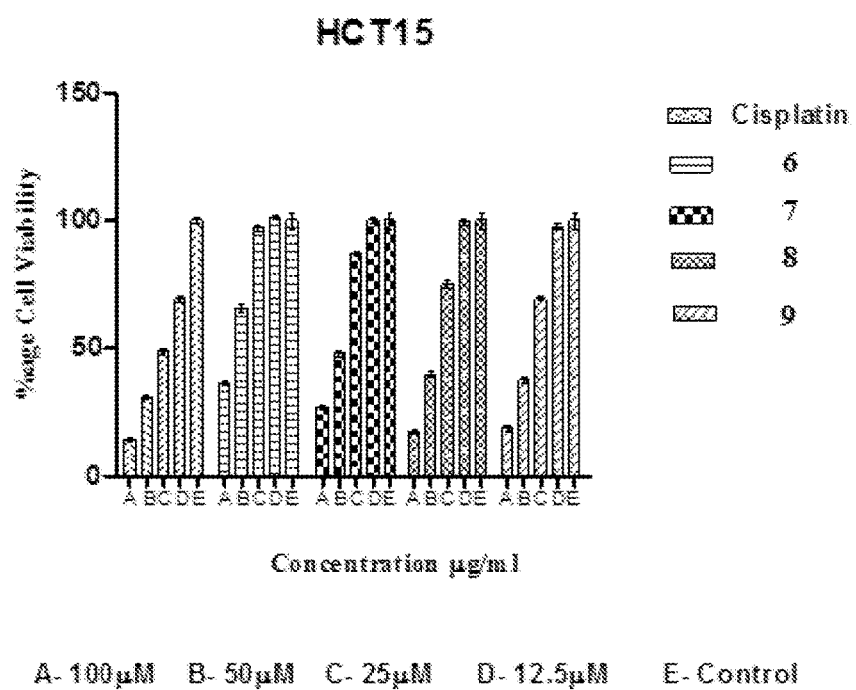

The survival of the cells (A549, MCF7 and HCTIS5) as a function of concentration of compounds Complex 1-Complex 9 is explained in FIGS. 5-7. The $IC_{50}$ values shown in Table 7 were obtained from the curves of the concentration of the complexes and percentage viability of the cells.

TABLE 4

$^{13}C$ NMR chemical shifts (ppm) of the ligands and their Pt(II) complexes in DMSO

| Species | C-2 | C-4 | C-5 | C-6 | C-7 | N—C1 | N—C2, N—C3 |
|---|---|---|---|---|---|---|---|
| Imt | 182.11 | 45.38 | 45.38 | — | — | — | — |
| 1 | 175.74 | 45.76 | 45.76 | — | — | — | — |
| MeImt | 181.38 | 42.00 | 51.82 | — | — | 34.35 | — |
| 2 | 174.90 | 42.76 | 52.65 | — | — | 34.02 | — |
| $Me_2Imt$ | 180.46 | 48.77 | 48.77 | — | — | 34.91 | — |
| 3 | 166.89 | 50.29 | 50.29 | — | — | 36.07 | — |
| $Et_2Imt$ | 178.74 | 46.13 | 46.13 | — | — | 42.69 | 11.92 |
| 4 | 170.96 | 47.33 | 47.33 | — | — | 43.79 | 12.11 |
| PrImt | 180.87 | 49.14 | 48.86 | | | 42.11 | 20.65, 11.09 |
| 5 | 174.50 | 50.10 | 49.10 | | | 42.82 | 20.53, 10.95 |
| iPrImt | 179.70 | 43.73 | 42.21 | — | — | 48.18 | 19.24 |
| 6 | 174.17 | 44.65 | 42.71 | | | 48.78 | 19.18 |
| $iPr_2Imt$ | 174.05 | 1.52 | 41.52 | — | — | 48.25 | 19.10 |
| 7 | 169.42 | 42.30 | 42.30 | | | 49.68 | 19.26 |
| EtDiaz | 173.26 | 46.48 | 20.83 | 41.04 | | 49.41 | 12.33 |
| 8 | 167.43 | 47.32 | 20.27 | 41.09 | | 49.67 | 12.19 |
| Diap | 183.99 | 45.86 | 26.99 | 26.99 | 45.86 | — | — |
| 9 | 176.53 | 46.35 | 26.51 | 26.51 | 46.35 | — | — |

Example 6

In Vitro Cytotoxic Activity Against AS549, MCF7 and HTC15 Human Cancer Cell Lines The trans-$[Pt(NH_3)_2(thione)_2].2NO_3$ complexes were evaluated for in vitro cytotoxic activity against A549 (human lung cancer), MCF-7 (human breast cancer) and HTC15 (human colon cancer) cell lines. The cells were seeded at $4 \times 10^3$ cells/well in 100 µL DMEM containing 10% FBS in 96-wells tissue culture plate and incubated for 72 h at 37° C., 5% $CO_2$ in air and 90% relative humidity in $CO_2$ incubator. After incubation, 100 µL of each sample solution (50, 25, 12.5 and 6.25 µM), prepared in DMEM, were added to cells and the cultures were incubated for 24 h. The medium of wells was discarded and 100 µL DMEM containing MTT (3-(4,5-Dimethylthiazol-2-yl)-2,5-diphenyltetrazolium Bromide) (5 mg/mL) was added to the wells and incubated in $CO_2$ incubator at 37° C. in dark for 4 h. After incubation, purple colored formazan (artificial chromogenic dye, product of the reduction of water insoluble tetrazolium salts e.g., MMT by dehydrogenases and reductases) in the cells is produced and appeared as dark crystals in the bottom of the wells. The resultant crystals were solublized by adding 100 µL of DMSO in each well. The solution was thoroughly mixed to dissolve the formazan crystals, producing a purple solution. The absorbance of the 96-wells plate was taken at 570 nm with Labsystems Multiskan EX-Enzyme-linked immunosorbent assay (EX-ELISA) reader against a reagent blank. The $IC_{50}$ values were calculated from three independent experiments by generating an equation of logarithmic trend line of percentage cell viability against concentration of compounds in Microsoft excel.

The exposure of the cells to an increase in concentration of the complexes resulted in a dose dependent cytotoxic effect. This cytotoxic effect was obtained by the stipulated increase in the concentration of the complexes, cisplatin and carboplatin against the fixed number of human cancer cells.

The $IC_{50}$ values of the complexes for A549 cell line range between 40 to 75 µM. Complexes 2 and 5 have in vitro cytotoxicity better than cisplatin with $IC_{50}$ values 40 and 41 µM respectively, and almost two-fold better than that of carboplatin. Complexes 1, 6, 8 and 9 have in vitro cytotoxicity slightly lower than cisplatin but still higher than carboplatin. Complexes 3 and 7 have the same cytotoxicity as carboplatin.

The $IC_{50}$ values of the complexes for the MCF7 cell line range are between 45 and 92 µM as shown by Table 4. Only the Complexes 5 and 8 were found to have cytotoxicity against the MCF7 cell line between cisplatin and carboplatin. While the others displayed poor antiproliferative potency as indicated by their higher $IC_{50}$ values.

Against HCTIS5 cell line, the Complexes 2, 5, 8 and 9 have activity comparable to cisplatin with $IC_{50}$ values 40, 36, 43, and 41 µM respectively. The Complex 1 and Complex 7 have almost the same cytotoxicity as carboplatin, while Complexes 3, 4 and 6 are less potent even than carboplatin.

These results are consistent with a significant selective cytotoxicity of the complexes against particular cancer cell lines and its tendency to undergo ligand exchange with biomolecules like proteins and DNA.

TABLE 5

$IC_{50}$ Values (in µM) of Pt(II) compounds against three human tumor cell lines

| Compounds | A549 | MCF7 | HCT15 |
|---|---|---|---|
| Cisplatin | 42 ± 2 | 23 ± 3 | 32 ± 2 |
| Carboplatin | 70 ± 2 | 63 ± 2 | 53 ± 2 |
| 1 | 52 ± 2 | 80 ± 1 | 50 ± 1 |
| 2 | 40 ± 1 | 70 ± 1 | 40 ± 2 |
| 3 | 70 ± 1 | 92 ± 2 | 69 ± 2 |
| 4 | 75 ± 1 | 89 ± 1 | 63 ± 1 |
| 5 | 41 ± 2 | 45 ± 1 | 36 ± 1 |
| 6 | 66 ± 2 | 86 ± 2 | 79 ± 1 |

TABLE 5-continued

IC$_{50}$ Values (in µM) of Pt(II) compounds against three human tumor cell lines

| Compounds | A549 | MCF7 | HCT15 |
|---|---|---|---|
| 7 | 69 ± 1 | 87 ± 2 | 53 ± 1 |
| 8 | 48 ± 1 | 60 ± 2 | 43 ± 1 |
| 9 | 49 ± 1 | 69 ± 1 | 41 ± 2 |

The experimental results are presented as the micro-mole concentration of 50% cell growth inhibition (IC$_{50}$) of each drug. The MTT assay was performed in three independent experiments, each in triplicate. The cancer cell lines used are A549 (human lung cancer), MCF-7 (human breast cancer) and HTC15 (human colon cancer) cell lines. Errors are standard deviations determined from at least three independent experiments.

As apparent from the Examples, transplatin-based Complexes 1-9 with the general formulae, trans-[Pt(NH$_3$)$_2$(Thione)$_2$]·2NO$_3$ can be successfully synthesized and characterized using analytical methods and exhibit cytotoxic activity against at least three different kinds of human cancer cells. The Complexes 2 and 5 exhibited a better cytotoxicity against A549 cancer cell line than cisplatin.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the words "a" and "an" and the like carry the meaning of "one or more" unless the context clearly indicates otherwise.

Within the description of this disclosure, where a numerical limit or range is stated, the endpoints are included unless stated otherwise. Also, all values and subranges within a numerical limit or range are specifically included as if explicitly written out. For example, a range of 0 to 10 wt % includes 0. 0.25, 0.5, 1, 1.5, 2, 2.5, 3, 4, 5, 6, 7, 8, 9, 9.75, 9.99, <10, and 10.

The terms "including", "such as", "for example" and the like not intended to limit the scope of the present disclosure. They generally refer to one or more elements falling with a class or genus of other similar elements.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

Links are disabled by insertion of a space or underlined space into a link, for example, before "www" or after "//" and may be reactivated by removal of the space.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all subranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z.

Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it is also envisioned that Parameter X may have other ranges of values including 1-9, 2-9, 3-8, 1-8, 1-3, 1-2, 2-10, 2.5-7.8, 2-8, 2-3, 3-10, and 3-9, as mere examples.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for inhibiting cell growth or proliferation, comprising:
    administering a chemotheraputic treatment to a subject having breast or lung cancer,
    contacting a neoplastic eukaryotic cell of the subject with a pharmaceutical composition comprising a platinum (II) thione complex represented by Formula (1):

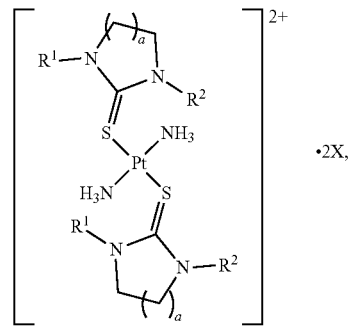

wherein $R^1$ and $R^2$ are each, independently, a hydrogen or a $C_1$-$C_3$ alkyl group, a is 1, 2 or 3; and X is nitrate, fluoride, chloride, bromide, iodide, or acetate.

2. The method of claim 1 that comprises administering, to the subject, trans-[Pt(NH$_3$)$_2$(Imt)$_2$].2NO$_3$ (Complex 1), trans-[Pt(NH$_3$)$_2$(MeImt)$_2$]. 2NO$_3$ (Complex 2), trans-[Pt(NH$_3$)$_2$(Me$_2$Imt)$_2$]. 2NO$_3$ (Complex 3), trans-[Pt(NH$_3$)$_2$(Et$_2$Imt)$_2$]. 2NO$_3$ (Complex 4), trans-[Pt(NH$_3$)$_2$(PrImt)$_2$]. 2NO$_3$ (Complex 5), trans-[Pt(NH$_3$)$_2$(iPrImt)$_2$]. 2NO$_3$ (Complex 6), or trans-[Pt(NH$_3$)$_2$(iPr$_2$Imt)$_2$].2 NO$_3$ (Complex 7).

3. The method of claim 1 that comprises administering, to the subject, trans-[Pt(NH$_3$)$_2$(EtDiaz)$_2$]. 2NO$_3$ (Complex 8).

4. The method of claim 1 that comprises administering, to the subject, trans-[Pt(NH$_3$)$_2$(Diap)$_2$]. 2NO$_3$(Complex 9).

5. The method of claim 1, wherein the platinum(II) thione complex is administered, to the subject, parenterally.

6. The method of claim 1, wherein the pharmaceutical composition is administered, to the subject, intravenously.

7. The method of claim 1, wherein the platinum(II) thione complex is administered, to the subject, into a tumor or into a site infiltrated by cancer cells.

* * * * *